(12) United States Patent
Willis et al.

(10) Patent No.: US 9,731,139 B2
(45) Date of Patent: Aug. 15, 2017

(54) LOCAL LEAD TO IMPROVE ENERGY EFFICIENCY IN IMPLANTABLE WIRELESS ACOUSTIC STIMULATORS

(71) Applicant: EBR Systems, Inc., Sunnyvale, CA (US)

(72) Inventors: Nathanial P. Willis, Atherton, CA (US); Richard E. Riley, Palo Alto, CA (US); Mark W. Cowan, San Jose, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

(21) Appl. No.: 14/979,359

(22) Filed: Dec. 22, 2015

(65) Prior Publication Data

US 2016/0114176 A1  Apr. 28, 2016

Related U.S. Application Data

(62) Division of application No. 12/174,509, filed on Jul. 16, 2008, now abandoned.

(51) Int. Cl.
*A61N 1/372* (2006.01)
*A61N 1/05* (2006.01)
(Continued)

(52) U.S. Cl.
CPC ......... *A61N 1/37217* (2013.01); *A61N 1/056* (2013.01); *A61N 1/0587* (2013.01);
(Continued)

(58) Field of Classification Search
CPC ............................ A61N 1/3756; A61N 1/3787
See application file for complete search history.

(56) References Cited

U.S. PATENT DOCUMENTS 3,204,637 A  9/1965 Frank et al.
3,659,615 A  5/1972 Enger
(Continued)

FOREIGN PATENT DOCUMENTS

DE        4330680 A1     3/1995
WO     WO-9961058 A1   12/1999
(Continued)

OTHER PUBLICATIONS

Abraham et al., for the MIRACLE study group, "Cardiac Resynchronization in Chronic Heart Failure," N Engl J Med, 2002;346:1845-53.
(Continued)

*Primary Examiner* — Allen Porter, Jr.
(74) *Attorney, Agent, or Firm* — Wilson Sonsini Goodrich & Rosati

(57) ABSTRACT

A wireless cardiac stimulation device is disclosed comprising a controller-transmitter, a receiver, and a stimulating electrode, wherein the stimulating electrode and the receiver are separately implantable at cardiac tissue locations of the heart and are connected by a local lead. Having separately implantable receiver and stimulating electrodes improves the efficiency of ultrasound mediated wireless stimulation by allowing the receiver to be placed optimally for reception efficiency, thereby resulting in longer battery life, and by allowing the stimulating electrode to be placed optimally for stimulus delivery. Another advantage is a reduced risk of embolization, since the receiver and stimulating electrode ensemble is attached at two locations of the heart wall, with the connecting local leads serving as a safety tether should either the receiver or the stimulating electrode become dislodged.

6 Claims, 9 Drawing Sheets

(51) Int. Cl.
- *A61N 1/378* (2006.01)
- *A61N 1/362* (2006.01)
- *A61N 1/368* (2006.01)
- *A61N 1/375* (2006.01)

(52) U.S. Cl.
CPC ............ *A61N 1/362* (2013.01); *A61N 1/3787* (2013.01); *A61N 1/3684* (2013.01); *A61N 1/3756* (2013.01); *A61N 1/37205* (2013.01)

(56) References Cited

U.S. PATENT DOCUMENTS

| | | |
|---|---|---|
| 3,693,627 A | 9/1972 | Berkovits |
| 3,698,398 A | 10/1972 | Berkovits |
| 3,735,756 A | 5/1973 | Richards et al. |
| 3,832,994 A | 9/1974 | Bicher et al. |
| 3,857,382 A | 12/1974 | Williams et al. |
| 3,939,844 A | 2/1976 | Pequignot |
| 3,942,534 A | 3/1976 | Allen et al. |
| 3,943,936 A | 3/1976 | Rasor et al. |
| 4,026,304 A | 5/1977 | Levy |
| 4,041,954 A | 8/1977 | Ohara |
| 4,181,133 A | 1/1980 | Kolenik et al. |
| 4,256,115 A | 3/1981 | Bilitch |
| 4,265,228 A | 5/1981 | Zoll |
| 4,280,502 A | 7/1981 | Baker, Jr. et al. |
| 4,333,469 A | 6/1982 | Jeffcoat et al. |
| 4,530,360 A | 7/1985 | Duarte |
| 4,561,442 A | 12/1985 | Vollmann et al. |
| 4,561,443 A | 12/1985 | Hogrefe et al. |
| 4,577,633 A | 3/1986 | Berkovits et al. |
| 4,651,716 A | 3/1987 | Forester et al. |
| 4,690,144 A | 9/1987 | Rise et al. |
| 4,830,006 A | 5/1989 | Haluska et al. |
| 5,018,523 A | 5/1991 | Bach, Jr. et al. |
| 5,063,928 A | 11/1991 | Grevis et al. |
| 5,103,129 A | 4/1992 | Slayton et al. |
| 5,113,859 A | 5/1992 | Funke |
| 5,165,403 A | 11/1992 | Mehra |
| 5,170,784 A | 12/1992 | Ramon et al. |
| 5,174,289 A | 12/1992 | Cohen |
| 5,193,539 A | 3/1993 | Schulman et al. |
| 5,292,338 A | 3/1994 | Bardy |
| 5,309,898 A | 5/1994 | Kaufman et al. |
| 5,377,166 A | 12/1994 | Kuhn |
| 5,405,367 A | 4/1995 | Schulman et al. |
| 5,411,535 A | 5/1995 | Fujii et al. |
| 5,433,731 A | 7/1995 | Hoegnelid et al. |
| 5,441,527 A | 8/1995 | Erickson et al. |
| 5,496,256 A | 3/1996 | Bock et al. |
| 5,547,459 A | 8/1996 | Kaufman et al. |
| 5,556,372 A | 9/1996 | Talish et al. |
| 5,674,251 A | 10/1997 | Combs et al. |
| 5,749,909 A | 5/1998 | Schroeppel et al. |
| 5,751,539 A | 5/1998 | Stevenson et al. |
| 5,752,924 A | 5/1998 | Kaufman et al. |
| 5,757,104 A | 5/1998 | Getman et al. |
| 5,766,227 A | 6/1998 | Nappholz et al. |
| 5,800,464 A | 9/1998 | Kieval |
| 5,814,089 A | 9/1998 | Stokes et al. |
| 5,817,130 A | 10/1998 | Cox et al. |
| 5,844,349 A | 12/1998 | Oakley et al. |
| 5,861,018 A | 1/1999 | Feierbach |
| 5,871,506 A | 2/1999 | Mower |
| 5,935,158 A | 8/1999 | Holmstrom et al. |
| 5,978,204 A | 11/1999 | Stevenson |
| 5,998,910 A | 12/1999 | Park et al. |
| 6,037,704 A | 3/2000 | Welle |
| 6,070,101 A | 5/2000 | Struble et al. |
| 6,078,837 A | 6/2000 | Peterson et al. |
| 6,110,098 A | 8/2000 | Renirie et al. |
| 6,141,588 A | 10/2000 | Cox et al. |
| 6,185,452 B1 | 2/2001 | Schulman et al. |
| 6,208,894 B1 | 3/2001 | Schulman et al. |
| 6,223,079 B1 | 4/2001 | Bakels et al. |
| 6,231,528 B1 | 5/2001 | Kaufman et al. |
| 6,233,484 B1 | 5/2001 | Ben-Haim et al. |
| 6,322,527 B1 | 11/2001 | Talish |
| 6,330,475 B1 | 12/2001 | Renirie et al. |
| 6,366,816 B1 | 4/2002 | Marchesi |
| 6,381,493 B1 | 4/2002 | Stadler et al. |
| 6,408,205 B1 | 6/2002 | Renirie et al. |
| 6,424,234 B1 | 7/2002 | Stevenson |
| 6,439,236 B1 | 8/2002 | Porter et al. |
| 6,445,953 B1 | 9/2002 | Bulkes et al. |
| 6,534,895 B2 | 3/2003 | Kadota et al. |
| RE38,119 E | 5/2003 | Mower |
| 6,628,989 B1 | 9/2003 | Penner et al. |
| 6,645,145 B1 | 11/2003 | Dreschel et al. |
| 6,647,292 B1 | 11/2003 | Bardy et al. |
| 6,652,473 B2 | 11/2003 | Kaufman et al. |
| 6,654,638 B1 | 11/2003 | Sweeney |
| 6,671,547 B2 | 12/2003 | Lyster et al. |
| 6,707,230 B2 | 3/2004 | Smith et al. |
| 6,721,597 B1 | 4/2004 | Bardy et al. |
| 6,754,528 B2 | 6/2004 | Bardy et al. |
| 6,754,531 B1 | 6/2004 | Kroll et al. |
| 6,764,446 B2 | 7/2004 | Wolinsky et al. |
| 6,788,974 B2 | 9/2004 | Bardy et al. |
| 6,798,716 B1 | 9/2004 | Charych |
| 6,834,204 B2 | 12/2004 | Ostroff et al. |
| 6,856,835 B2 | 2/2005 | Bardy et al. |
| 6,970,742 B2 | 11/2005 | Mann et al. |
| 6,983,185 B2 | 1/2006 | Ley et al. |
| 7,010,350 B2 | 3/2006 | Kralik |
| 7,024,248 B2 | 4/2006 | Penner et al. |
| 7,198,603 B2 | 4/2007 | Penner et al. |
| 7,200,437 B1 | 4/2007 | Nabutovsky et al. |
| 7,283,874 B2 | 10/2007 | Penner |
| 7,610,092 B2 | 10/2009 | Cowan et al. |
| 7,930,031 B2 | 4/2011 | Penner |
| 2004/0015104 A1 | 1/2004 | Goldberger |
| 2004/0138516 A1 | 7/2004 | Osorio et al. |
| 2004/0147973 A1 | 7/2004 | Hauser |
| 2004/0172083 A1 | 9/2004 | Penner |
| 2004/0243192 A1 | 12/2004 | Hepp et al. |
| 2004/0260214 A1 | 12/2004 | Echt et al. |
| 2005/0055056 A1 | 3/2005 | Olson |
| 2005/0096702 A1* | 5/2005 | Denker ............ A61N 1/05 607/9 |
| 2005/0288756 A1 | 12/2005 | Gray |
| 2006/0136004 A1 | 6/2006 | Cowan et al. |
| 2006/0136005 A1 | 6/2006 | Brisken et al. |
| 2007/0027508 A1 | 2/2007 | Cowan |
| 2007/0055184 A1 | 3/2007 | Echt et al. |
| 2007/0060961 A1 | 3/2007 | Echt et al. |
| 2007/0078490 A1 | 4/2007 | Cowan et al. |
| 2008/0294208 A1 | 11/2008 | Willis et al. |
| 2010/0016911 A1 | 1/2010 | Willis et al. |

FOREIGN PATENT DOCUMENTS

| | | |
|---|---|---|
| WO | WO-03070323 A1 | 8/2003 |
| WO | WO-2007149936 A2 | 12/2007 |
| WO | WO-2007149936 A3 | 10/2008 |

OTHER PUBLICATIONS

ACC/AHA Task Force on Practice Guidelines, "Evaluation and Management of Chronic Heart Failure in the Adult," JACC 2002;38:2101-13.

Allessie et al., "Regional Control of Atrial Fibrillation by Rapid Pacing in Conscious Dogs," Circulation 1991;84:1689-97.

Ansalone et al., "Bi-ventricular Pacing I Heart Failure:Back to Basics in the Pathophysiology of Left Bundle Branch Block to Reduce the Number of Nonresponders," Am J Cardiol 2003;91:55F-61F.

Auricchio et al., "Cardiac Resynchronization Therapy: Current State of the Art," Circulation 2004;109:300-307.

Bardy, et al. The Totally Subcutaneous ICD System (The S-ICD). PACE. 2002; 24,578.

(56) References Cited

OTHER PUBLICATIONS

Becker et al, "Suppression of Atrial Fibrillation by Multisite and Septal Pacing in a Novel Experimental Model", Cardiovascular Research 2001;54(2):476-481.
Bradley, et al. Cardiac resynchronization and death from progressive heart failure: a meta-analysis of randomized controlled trials. JAMA. Feb. 12, 2003;289(6):730-40.
Camm, et al. Chapter 6: Nonpharmaceutical treatment of atrial fibrillation, In Atrial Fibrillation. Facts from Yesterday—Ideas for tomorrow. Futura Publishing Company, Inc., Armonk, NY, 1994, pp. 125-147.
Dalecki, et al. Effects of Pulsed Ultrasound on the Frog Heart: I. Thresholds for Changes in Cardiac Rhythm and Aortic Pressure. Ultrasound in Med. & Biol. 1993; 19:385-390.
Dalecki et al., "Effects of Pulsed Ultrasound on the Frog Heart: II. An Investigation of Heating as a Potential Mechanism," Ultrasound in Med. & Biol. 1993; 19:391-398.
Dalecki et al., "Thresholds for premature ventricular contractions in frog hearts exposed to lithotripter fields," Ultrasound in Med. & Biol. 1991; 17:341-346.
Daoud, et al. Implantation techniques and chronic lead parameters of biventricular pacing dual-chamber defibrillators. J Cardiovasc Electrophysiol. Oct. 2002;13(10):964-70.
Daubert, et al. Permanent left ventricular pacing with transvenous leads inserted into the coronary veins. Pacing Clin Electrophysiol. Jan. 1998;21(1 Pt 2):239-45.
Daubert, et al. Use of Specifically Designed Coronary Sinus Leads for Permanent Left Ventricular Pacing: Preliminary Experience. PACE, 1997; 20: II-NASPE Abstract 17, Apr. 1997.
David Trial Investigators, The Dual Chamber and WI Implantable Defibrillator (DAVID) Trial, JAMA 2002;288:3115-3123.
Deshmukh et al. "Direct His-bundle pacing: present and future," PACE 2004;27 [Pt.II]:862-70.
Ellenbogen et al., "Detection and Management of An Implantable Cardioverter Defibrillator Lead Failure," JACC. 2003;41:73-80.
Feldman et al, "Comparison of medical therapy, resynchronization and defibrillation therapies in heart failure trial (COMPANION)," Presented at ACC 2003 Late Breaking Clinical Trials, 1 page.
Franz, "Mechano-electrical feedback in ventricular myocardium," Cardiovascular Research. 1996; 32:15-24.
Gregoratos, et al. ACC/AHA/NASPE 2002 guideline update for implantation of cardiac pacemakers and antiarrhythmia devices: a report of the American College of Cardiology/American Heart Association Task Force on Practice Guidelines (ACC/AHA/NASPE Committee to Update the 1998 Pacemaker Guidelines). Circulation. 2002; 106:2145-2161.
Heckman et al., "Acceleration of tibial fracture-healing by non-invasive, low-intensity pulsed ultrasound" The Journal of Bone and Joint Surgery, vol. 76, Issue 1, pp. 26-34, 1994.
Hu et al., "Stretch-Activated Ion Channels in the Heart," J. Mot. Cell Cardiol. 1997; 29:1511-1523.
Johnson et al., "Adaptive Pacing During Ventricular Fibrillation," PACE 2003;26:1824-36.
Kalman J.M. et al, "Regional Entrainment of Atrial Fibrillation in Man", J Cardiovasc Electrophysiol 1991;7:867-76.
Kass et al., "Improved Left Ventricular Mechanics from Acute VDD Pacing in Patients with Dilated Cardiomyopathy and Ventricular Conduction Delay," Circulation 1999;99:1567-73.
Kenknight, et al. Regional Capture of Fibrillating Ventricular Myocardium. Circ Res 1999;77:849-55.retrieve from the Internet: circres.ahajournals.org/cgi/content/full/77/4/849.
Kohl et al., Stretch-Induced Changes in Heart Rate and Rhythm: Clinical Observations, Experiments and Mathematical Models. Progress in Biophysics & Molecular Biology, 1999; 71:91-138.
Kohl et al., "Sudden Cardiac Death by Commotio Cordis: Role of Mechano-Electrical Feedback," Cardiovascular Research, 2001; 50:280-289.
Leclercq, et al. Is Dual Site Better than Single Site Atrial Pacing in the Prevention of Atrial Fibrillation? PACE 2000;23:2102-7.
Leclercq et al., "Systolic Improvement and Mechanical Resynchronization does not Require Electrical Synchrony in the Dilated Failing Heart with Left Bundle-Branch Block", Circulation 2002;106:1760-1763.
Leclerq, et al. Acute Hemodynamic Effects of Biventricular DDD Pacing in Patients with End-Stage Heart Failure. JACC 1998;32:1825-1831.
Lee et al., "Effect of implantable Defibrillators of Arrhythmic Events and Mortality in the Multicenter Unsustained Tachycardia Trial," Circulation. 2002; 106:233-238.
Linde et al., "Long-Term Benefits of Biventricular Pacing in Congestive Heart Failure: From the Muitisite Stimulation in Cardiomyopathy (MUSTIC) Study", J Am Coll Cardiol 2002;40:111-118.
Miracle Trial Investigators, "Combined Cardiac Resynchronization and Implantable Cardioversion Defibrillation in Advanced Heart Failure: the Miracle ICD Trial," JAMA 2003;289:2685-2694.
Mirza et al, "Biatrial Pacing for Paroxysmal Atrial Fibrillation", J Am Coll Cardiol 2002;40:457-463.
Moss et al., "Prophylactic Implantation of a Defibrillator in Patients with Myocardial Infarction and Reduced Ejection Fraction," N Engl J Med. 2002; 346:877-933.
Niehaus et al., "Non-Contact Cardiac Stimulation with Iocused Ultrasound Pulses," PACE 2003: 26:1023.
Nielsen et al., "A Randomized Comparison of Atrial and Dual-Chambered Pacing in 177 Consecutive Patients With Sick Sinus Syndrome," J Am Coll Cardiol 2003;42:614-623.
Nolte, et al. Mechanically Induced Ventricular Extrasystoles in the Isolated Perfused Guinea-Pig Heart. Arzneim.-Forsch/Drug Research. 1987; 37(11): 1025-1029.
Office action dated Nov. 21, 2011 for U.S. Appl. No. 12/174,509.
Office action dated Feb. 6, 2015 for U.S. Appl. No. 12/174,509.
Office action dated Sep. 29, 2015 for U.S. Appl. No. 12/174,509.
Peschar et al., "Left Ventricular Septal and Apex Pacing for Optimal Pump Function in Canine Hearts," J Am Coll Cardiol, 2003;41:1218-26.
Reiter et al.., "Effects of Mechano-Electrical Feedback: Potential Arrhythmogenic Influence in Patients With Congestive Heart Failure," Cardiovascular Research, 1996; 32:44-51.
Smailys et al., "Investigation of the Possibilities of cardiac Defibrillation by Ultrasound," Resuscitation, 1981; 9:233-242.
Sowton, "Clinical Results with the Tachylog Antitachycardia Pacemaker", PACE 1984; 7(Part II):1313-1317.
Tacker. Chapter 1: Fibrillation causes and criteria for defibrillation. In Defibrillation of the Heart. Tacker, WA, ed. Mosby-Year Book, Inc., St. Louis, Missouri, 1994, pp. 1-14.
The Antiarrhythmics Versus Implantable Defibrillators (AVID) Investigators, "A Comparison of Antiarrhythmic Drug Therapy with Implantable Defibrillators in Patients Resuscitated from Near Fatal Ventricular Arrhythmias," N Engl J Med. 1997; 337:1576-1583.
Valls-Bertault et al., "Adverse Events with Transvenous Left Ventricular Pacing in Patients with Severe Heart Failure: Early Experience from a Single Centre," Europace, 2001;3:60-63.
Warren et al., "Clinical Evaluation of Automatic Tachycardia Diagnosis by an Implanted Device", PACE 1986;9 (Part II):1079-1083.

* cited by examiner

LOCAL LEAD TO IMPROVE ENERGY EFFICIENCY IN IMPLANTABLE WIRELESS ACOUSTIC STIMULATORS

CROSS-REFERENCE TO RELATED APPLICATIONS

This application is a divisional of U.S. patent application Ser. No. 12/174,509, filed Jul. 16, 2008, the entire content of which is incorporated herein by reference.

BACKGROUND OF THE INVENTION

1. Field of the Invention

The field of the present invention relates generally to implanted devices for tissue stimulation, monitoring, and other therapeutic or diagnostic functions, and specifically to implantable devices for the stimulation of cardiac tissue, for example pacemakers or implantable cardioverter-defibrillators (ICDs). More specifically, it pertains to such devices utilizing wireless energy transfer, for example through ultrasonic means.

2. Description of the Background Art

Conventional wired cardiac pacemaker and defibrillator systems comprise Implantable Pulse Generators (IPGs) configured to be located subcutaneously and connect via leads to stimulator electrodes implanted in the heart. However, because the IPG is connected to leads, the location and surgical process must consider lead insertion into a vascular access.

An ultrasound based wireless cardiac stimulation system has been disclosed in currently pending applications by the applicant (e.g., U.S. patent application Ser. No. 11/315,023). This system employs ultrasonic energy transfer from a subcutaneously implantable controller-transmitter device (C-T), which is directed towards one or more receiver-stimulator (R-S) devices implanted at desired sites in the heart, for example in the left ventricle. Ultrasonic transducers and circuitry in the R-S convert the transmitted ultrasonic energy into electrical energy capable of stimulating the cardiac tissue. The system, C-T, and R-S are described in co-pending U.S. patent applications Nos. (Publication Number) 20060136004, 20060136005, 20070027508, 20070055184, 20070078490 and 20070060961 and Ser. No. 11/752,775, which are herein incorporated by reference in their entirety.

Energy and battery life computations show that the range between the C-T and the R-S has a dramatic impact on the efficiency of energy transfer between them. Therefore, it is desirable to reduce the distance between the C-T and the R-S and thereby improve the efficiency of wireless pacing. An optimal location for cardiac stimulation is believed to be the posterio-lateral LV wall, and an optimal subdermal location for an IPG is the fifth intercostal space. These locations are approximately 10 cm apart. It is desirable to have a cardiac stimulation system that simultaneously optimizes the stimulation location and minimizes the wireless energy delivery range between the C-T and the R-S, thereby providing optimal battery life and optimal stimulation location. The present embodiments provide such a system.

SUMMARY OF THE INVENTION

Embodiments of the present invention are directed to wireless cardiac stimulation devices comprising a controller-transmitter (C-T), a receiver, and a stimulating electrode, wherein the stimulating electrode and the receiver are separately implantable at different locations of the heart and are connected by a local lead. Separating the receiver from the stimulating electrode improves the efficiency of ultrasound mediated wireless stimulation by allowing the receiver to be placed optimally for reception efficiency, thereby resulting in longer battery life or reduced battery size. Separation of the receiver and stimulating electrode also allows the stimulating electrode to be placed optimally for stimulus delivery, and provides for improved connective reliability.

In one aspect, the C-T is implanted subcutaneously such that its transmission passes through an intercostal space, and the receiver is implanted at the apex of the left ventricle (LV) of the heart, thereby minimizing the distance between the receiver and the C-T. The stimulating electrode is implanted, separately from the receiver, at an optimal posterio-lateral LV location, and connected to the receiver via a local lead for transfer of electrical energy. One advantage of such a system is the longer battery life due to the reduction in distance between the wireless transmitter and the receiver. Another advantage is a reduced risk of embolization, since the receiver and stimulating electrode are attached at two locations of the heart wall, with the connecting local lead serving as a safety tether should either the receiver or the stimulating electrode become dislodged.

In one aspect, the system comprises a plurality of stimulating electrodes, thereby providing multi-site stimulation. In another aspect, the receiver itself comprises a stimulating electrode, thereby providing dual-site stimulation. In another aspect, the receiver and stimulating electrode are implanted in different ventricles, thereby providing biventricular stimulation, with the local lead crossing the ventricular septum to connect the receiver and stimulating electrode.

Another aspect of the invention is methods of using acoustic energy to stimulate cardiac tissue by (a) subcutaneously implanting a transmitter; (b) implanting a receiver at a first cardiac tissue location, wherein the receiver receives acoustic energy transmitted by the transmitter and produces a biologically stimulating electrical output in response to the received acoustic energy; and (c) implanting a stimulating electrode at a second cardiac tissue location, wherein the stimulating electrode is connected to the receiver by a local lead, and wherein the stimulating electrode receives the biologically stimulating electrical output from the receiver and delivers said output to cardiac tissue. Additionally, the first cardiac tissue location can be chosen to optimize acoustic energy transmission from the transmitter to the receiver. Another embodiment of the above method involves implanting additional stimulating electrodes, wherein the stimulating electrodes are connected to the receiver by the local lead. Alternatively, the additional stimulating electrodes are connected to the receiver by additional local leads.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE EMBODIMENTS

Figure 1:
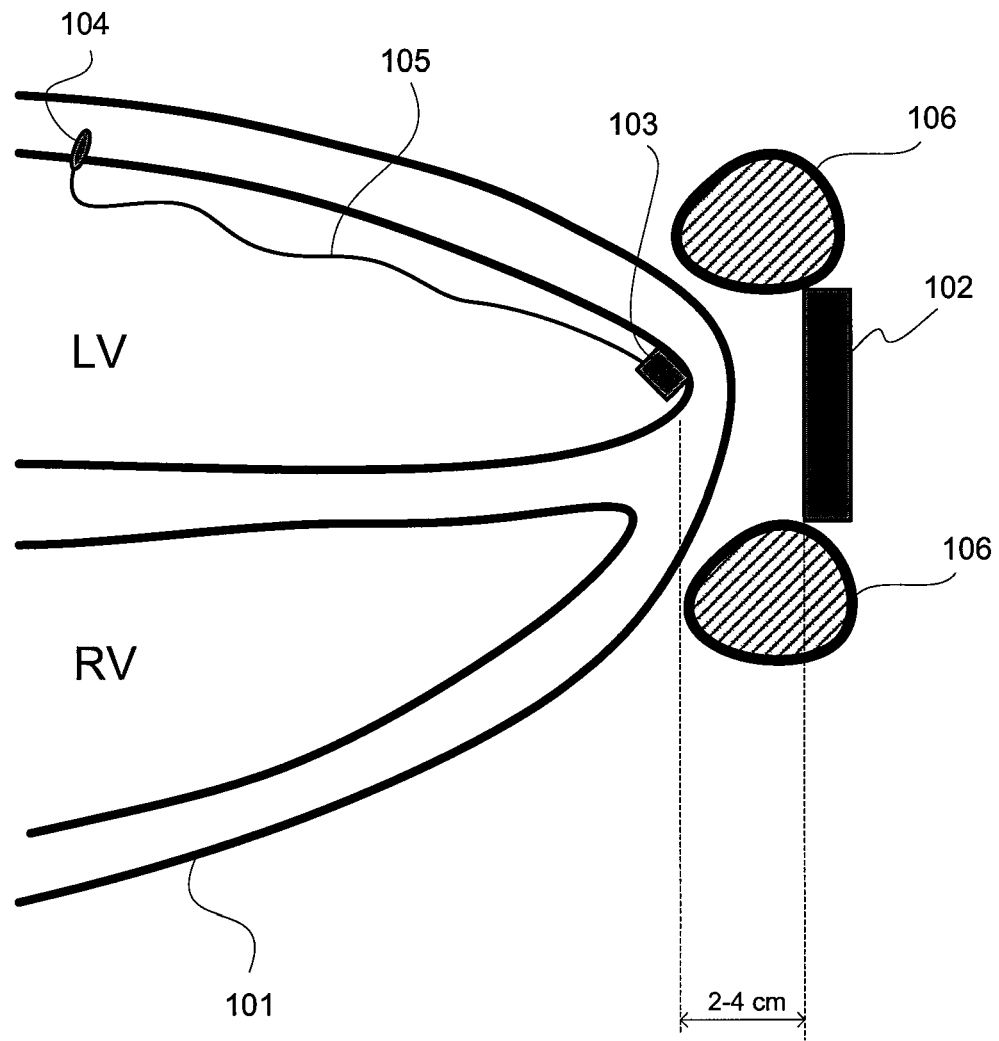
FIG. 1 shows an example embodiment of a system for electrically stimulating the heart, comprising separately implantable receiver and stimulating electrode implanted at endocardial locations of the heart wall.

In the following description, for purposes of explanation, numerous specific details are set forth in order to provide a thorough understanding of the invention. It will be apparent, however, to one skilled in the art that the invention can be practiced without these specific details.

An ultrasound based wireless cardiac stimulation system is disclosed which improves the efficiency of ultrasound mediated wireless stimulation and results in longer battery life. The system comprises two separately implantable subsystems. The first subsystem is a receiver-stimulator (R-S) configured to be implanted within the heart to provide electrical stimulation. The second subsystem is a controller-transmitter (C-T) configured to be implanted subcutaneously to wirelessly power and control the R-S.

To increase the operational efficiency and battery life of the system, the R-S itself comprises two separately implantable elements that are connected by a local lead. The first is an implantable receiver element (hereinafter also referred to as "receiver"), and the second is an implantable stimulating electrode element (hereinafter also referred to as "stimulating electrode"). The receiver wirelessly receives energy from the C-T, converts the received energy to electrical energy, and electrically powers the stimulating electrode via the local lead. The stimulating electrode receives the electrical energy and provides electrical stimulation to the tissue.

It is an advantageous aspect that the separation of the receiver from the stimulating electrode allows two goals to be simultaneously met. First, it allows the receiver to be implanted closest to the C-T, thereby minimizing the travel range of the wireless energy transmission from the C-T to the receiver. Second, it allows the stimulating electrode to be implanted at an optimal location within the heart for the delivery of electrical stimulation to heart tissue, independent of the location of the implanted receiver.

Reducing the distance between the C-T and the receiver allows more of the transmitted acoustic energy to be harvested by the receiver, since (a) less of the acoustic energy is spread to where the receiver cannot harvest it, providing a quadratic increase in gain as a function of the inverse of the distance between the C-T and the receiver, and (b) there is less intervening tissue between the C-T and the receiver that could lead to undesired energy dissipation. This means that the C-T needs to transmit less energy to achieve the same stimulation output. This provides not only a longer battery life, but also simpler C-T and receiver design, for example by using fewer transducers in the construction of the C-T and/or the receiver (such as only one transducer, in some embodiments).

Optionally, as disclosed in U.S. Patent Application Ser. No. 61/016,869, the C-T itself may comprise an implantable transmitter as well as a separately implantable battery for powering the transmitter via a subcutaneously routable electrical cable, thereby improving patient comfort and providing a larger usable aperture.

While the present embodiments refer to stimulating the heart, it is understood herein that the disclosed embodiments can be used to stimulate any living tissue in humans or animals. For example, published PCT application WO2007149936 with common inventor and assignee of this application, which is incorporated herein by reference, describes using a wireless stimulation system for stimulating various tissues.

FIG. 1 shows one embodiment of a system 100 for electrically stimulating the heart 101, comprising separately implantable receiver and stimulating electrode elements. The system 100 comprises a C-T 102, as well as an R-S comprising a receiver 103, a stimulating electrode 104, and a local lead 105 connecting the receiver 103 and stimulating electrode 104.

C-T 102 is configured to be implanted subcutaneously so as to be close to a location in the heart where the receiver 103 is to be implanted. In one embodiment, the C-T 102 is implanted subcutaneously such that its transmission passes through an intercostal space, such as the $5^{th}$ intercostal space. FIG. 1 shows C-T 102 implanted thusly, with the transmission passing through an intercostal space between ribs 106.

The receiver 103 is configured to be implanted at a location within the heart where it can be closest to the C-T 102. In one embodiment, the receiver 103 is implanted at the septal apex of the LV, as shown in FIG. 1. This could be done using traditional interventional techniques, wherein a delivery catheter is advanced percutaneously into the left ventricle and the receiver is delivered and fixed at a preferred site. The fixation could be accomplished using various tissue fixing mechanisms such as barbs, tines, etc.

In such an embodiment where the C-T 102 is implanted at an intercostal space and the receiver 103 is implanted at the septal apex of the LV, the distance between the C-T 102 and the receiver 103 is minimized to approximately 2-4 cm, allowing efficient energy transfer from the C-T 102 to the receiver 103, and therefore providing for longer battery life for C-T 102.

While FIG. 1 shows the receiver 103 and stimulation electrode 104 implanted at an endocardial location of the heart wall, in other embodiments one or both may be implanted at an epicardial location. Such an embodiment is shown in FIG. 2a, with the receiver 103 and stimulation electrode 104 implanted at epicardial locations.

Figure 2A:
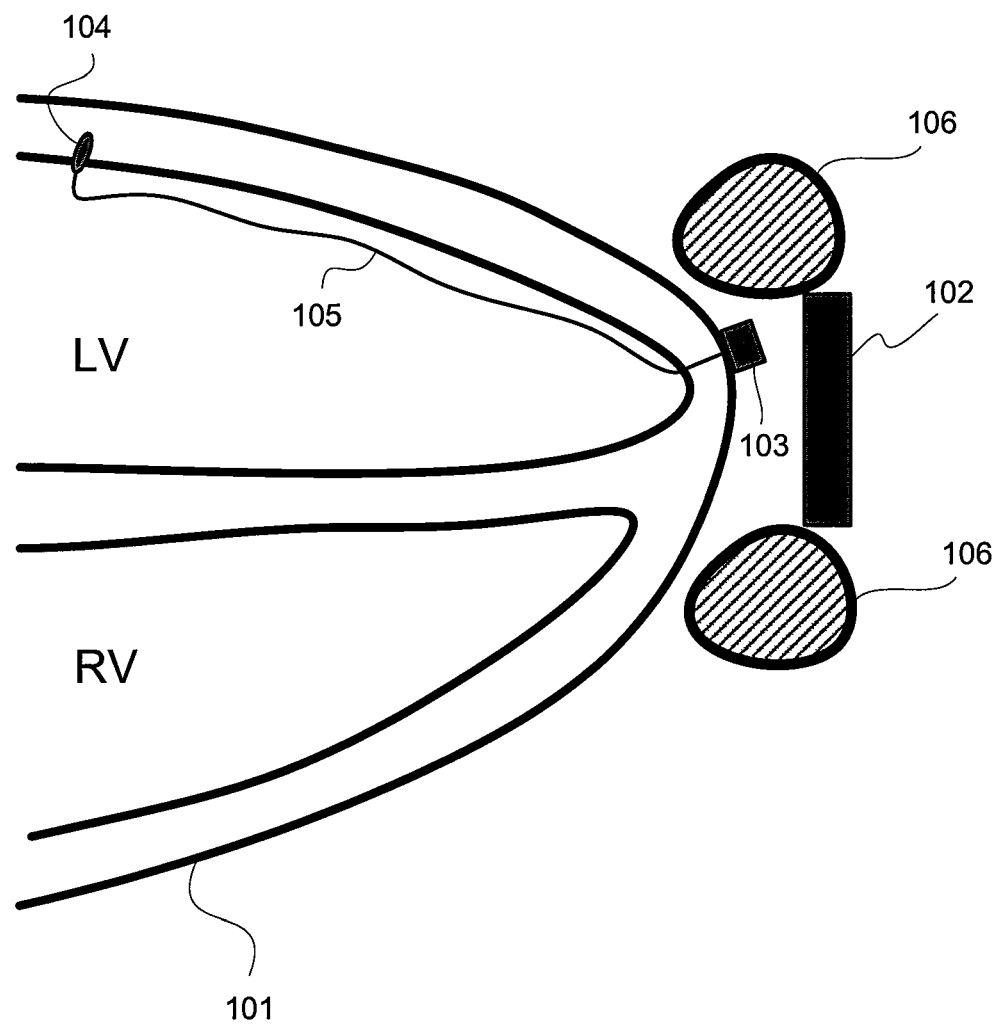
FIGS. 2a and 2b show other example embodiments of a system for electrically stimulating the heart, comprising a separately implantable receiver and/or stimulating electrode implanted at an epicardial location of the heart wall.
Figure 2B:
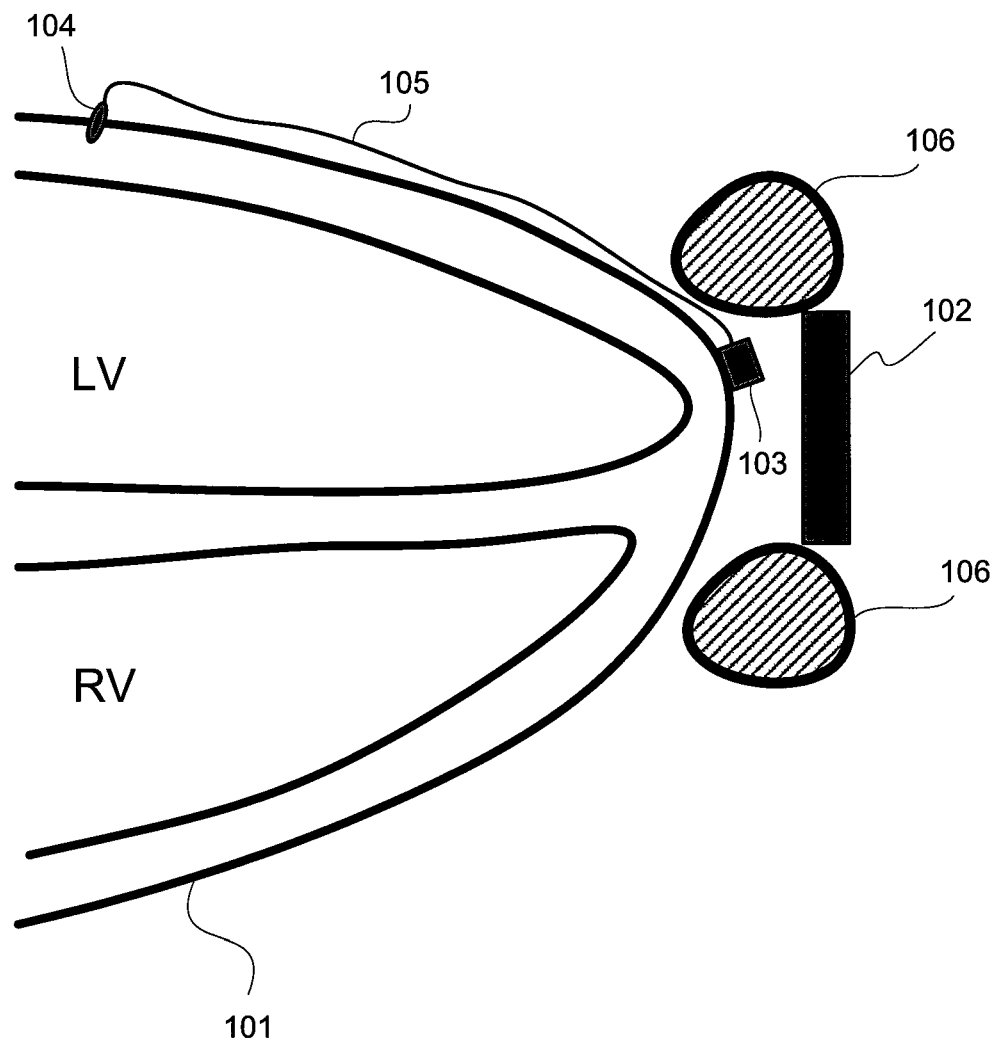

In one such embodiment, the receiver 103 can be placed on the anterior of the heart by using a minimally invasive surgical approach, as shown in FIG. 2a. Once the receiver 103 is fixed to the anterior surface of the heart and within the desired range of the C-T 102, a stimulating electrode 104 could be localized at an endocardial location by penetrating the stimulating electrode 104 through the heart wall 101 from the epicardial surface. A small diameter trocar or such implement could enable the implantation of the receiver 103 and the stimulating electrode 104 from the external surface (as opposed to interventional means). Alternatively, the stimulating electrode 104 may be placed at an epicardial location to provide stimulation (as shown in FIG. 2b).

Figure 3:
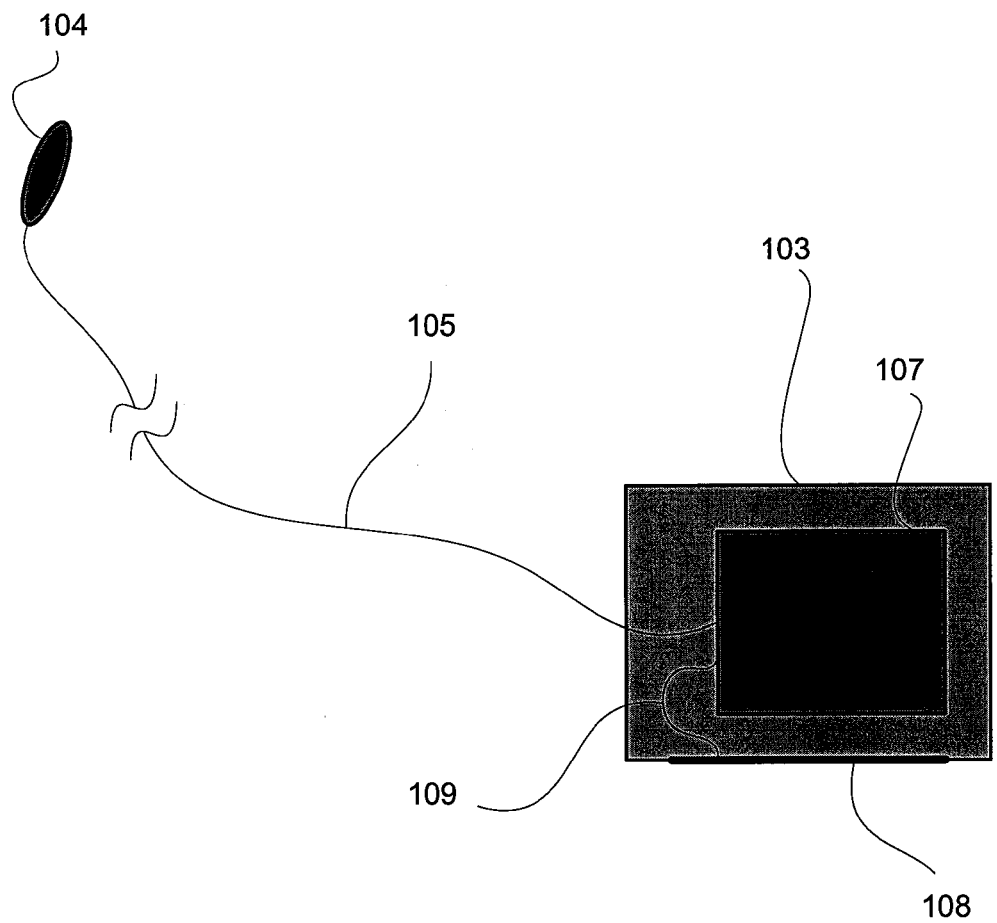
FIG. 3 shows an example embodiment of a receiver.

As shown in FIG. 3, the receiver 103 comprises internal circuitry 107 for converting acoustic energy to electrical energy that is transmitted to the stimulating electrode 104. In one embodiment, the circuitry 107 comprises one or more transducers which produce electrical energy in response to the acoustic energy received from the C-T 102. The transducers may comprise piezoelectric material, such as a polycrystalline ceramic piezoelectric material or a single crystal piezoelectric material.

Circuitry 107 further comprises one or more conversion circuits, wherein each conversion circuit is electrically connected to a corresponding transducer such that the electrical energy output from the transducers is converted to a biologically stimulating electrical output. For example, the conversion circuitry may comprise one or more rectifiers, as well as optional protection circuitry (such as comprising one or more Zener diodes) to protect the rectifiers from damage due to high voltages.

The stimulating electrode 104 is configured to be implanted at a cardiac tissue location, separately from the receiver 103, at a location that is optimal for delivering the stimulating electrical output to the heart. The stimulating electrode 104 comprises one or more electrodes (cathode) for delivering the electrical output to tissue, and is powered by the receiver 103 via a local lead 105. In one embodiment, as shown in FIG. 1, the stimulating electrode 104 is implanted at a posterio-lateral location in the LV. As shown in FIG. 3, the receiver 103 comprises an anode 108 electrically connected to circuitry 107 via an electrical connection 109. The anode 108 may comprise part or all of the exterior of the receiver 103 or alternatively may be placed anywhere along the length of the local lead (not shown). Typically, the anode is a large surface area electrode relative to the cathode having a low current density to preferentially stimulate the tissue at the cathode, in this embodiment at the stimulating electrode 104. Alternatively, the anode can be designed to have a small surface area to intentionally stimulate the tissue at the receiver location, thereby providing dual site stimulation from both the anode and cathode.

As described above, separating the implant locations of the receiver 103 and stimulating electrode 104 allows the system 100 to simultaneously optimize wireless energy transfer efficiency as well as stimulation location. Furthermore, separating the receiver 103 from the stimulating electrode 104 also reduces the risk of embolization, since the R-S ensemble is now attached at two locations in the heart wall, with the local lead 105 serving as a safety tether should either the receiver 103 or the stimulating electrode 104 become dislodged.

Optionally, the system 100 may be extended to provide multi-site stimulation. For example, the system 100 may comprise a plurality of stimulation electrodes to provide multi-site stimulation. In one such embodiment, the receiver 103 itself comprises a stimulation electrode, so that the heart is stimulated at the receiver 103 site in addition to stimulation provided at the stimulating electrode 104 site.

Figure 4A:
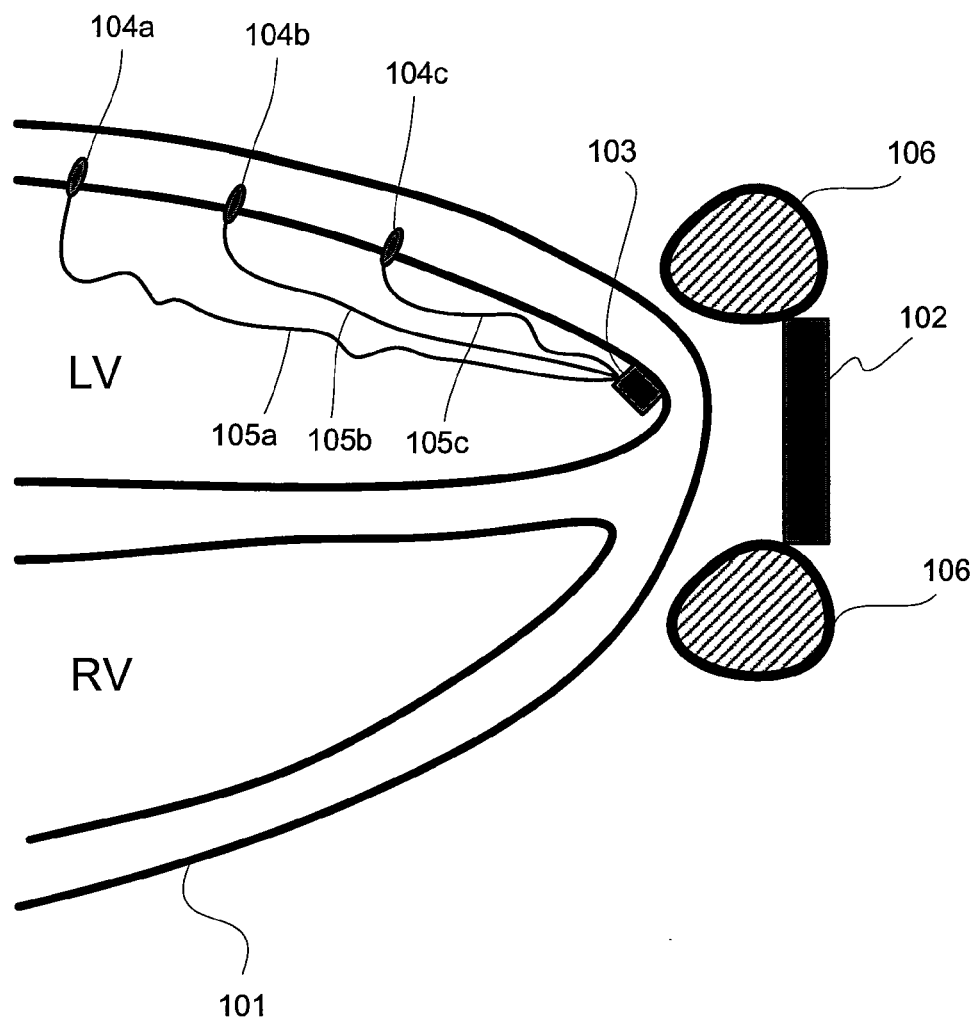
FIGS. 4a-4c show example embodiments of systems configured with a single receiver and a plurality of stimulating electrodes.
Figure 4B:
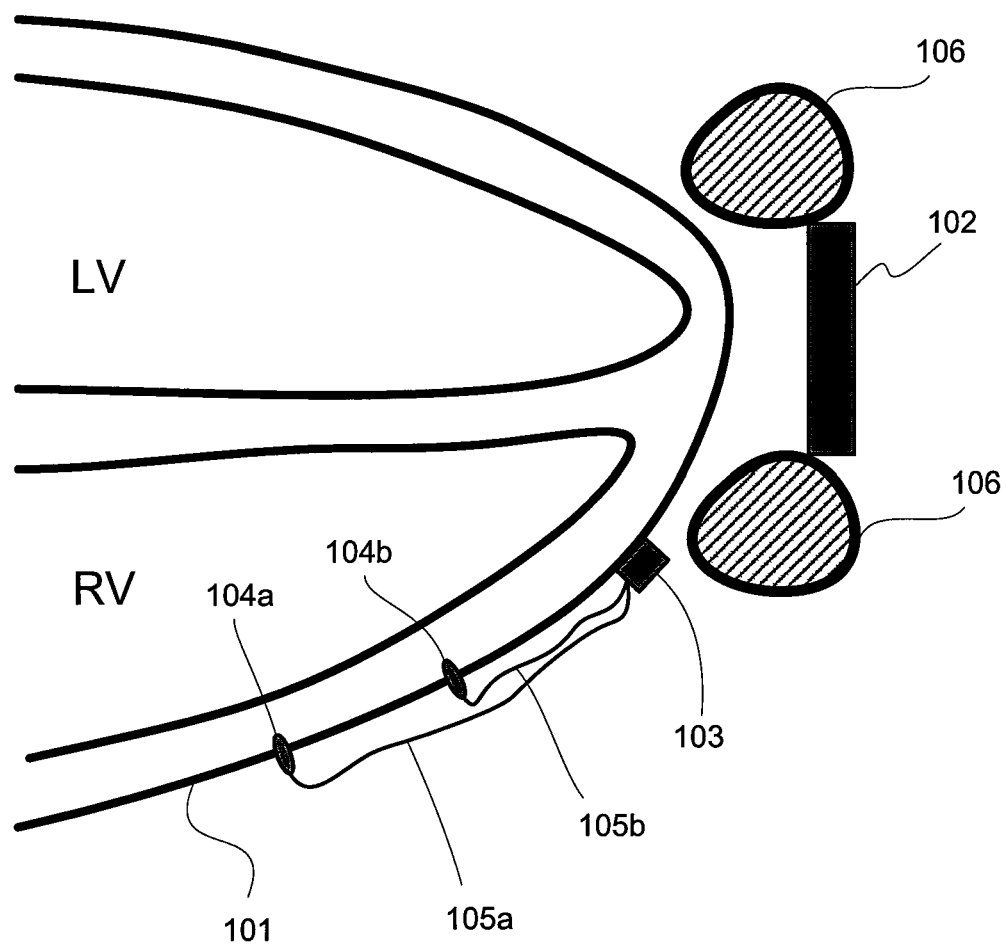
Figure 4C:
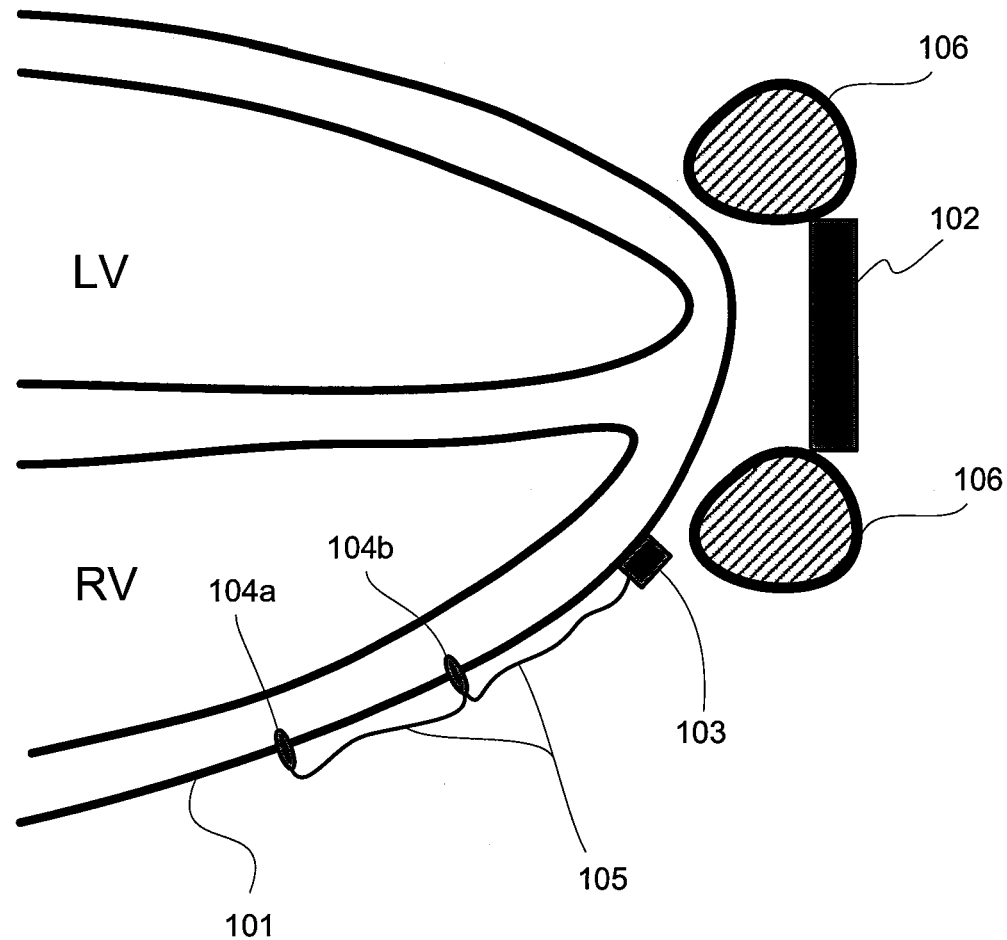

In another embodiment for multi-site stimulation, the system 100 comprises more than one stimulating electrode, each connected to the receiver 103 via a single or multiple local leads. FIG. 4a shows one such embodiment, wherein multiple stimulating electrodes 104a, 104b, and 104c (at endocardial locations of the heart) are connected via multiple local leads 105a, 105b, and 105c to a receiver 103 (also at an endocardial location), thereby providing multi-site stimulation. FIG. 4b shows another such embodiment, wherein multiple stimulating electrodes 104a and 104b (at epidardial locations) are connected via multiple local leads 105a and 105b to a receiver 103 (also at an epicardial location), thereby providing multi-site stimulation. Alternatively or in combination, two or more of the stimulating electrodes may be contained on a single local lead, such as shown in FIG. 4c with receiver 103 connected in series to stimulating electrodes 104a and 104b via local lead 105.

Figure 5:
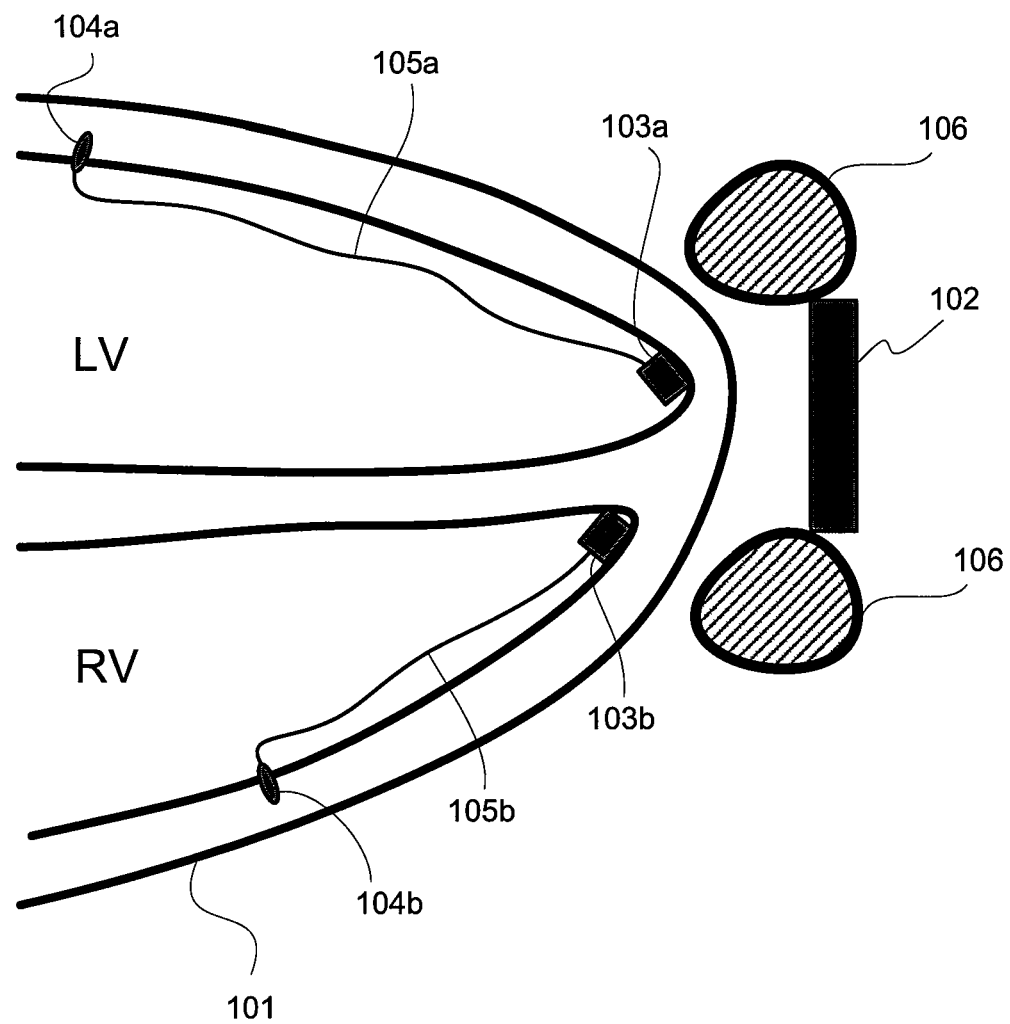
FIG. 5 shows an example embodiment of a system configured with a plurality of receivers and a plurality of stimulating electrodes.

In another embodiment for multi-site stimulation, the system 100 may be configured with a plurality of receivers. FIG. 5 shows one such embodiment, wherein a first receiver 103a is implanted at a cardiac tissue location of the LV and connected to a first stimulating electrode 104a via a first local lead 105a, and a second receiver 103b is implanted at a cardiac tissue location of the RV and connected to a second stimulating electrode 104b via a second local lead 105b. Analogously, system 100 may comprise more than two receivers, each of which may electrically power one or more stimulating electrodes via one or more local leads.

Optionally, the system 100 may be configured to provide biventricular stimulation. In one such embodiment, the receiver 103 comprises a stimulation electrode for providing electrical stimulation, and is implanted at a cardiac tissue location of the septal apex of the right ventricle (RV), allowing the receiver 103 to function as an RV lead for biventricular stimulation. In another embodiment, the receiver 103 may be implanted at a cardiac tissue location of the RV, with the local lead 105 having a very small profile (i.e. a small surface area lead) and puncturing through the ventricular septum to the LV and connecting the receiver 103 with one or more stimulating electrodes 104. Crossing the ventricular septum with such a small profile local lead would cause minimal to no trauma.

Figure 6:
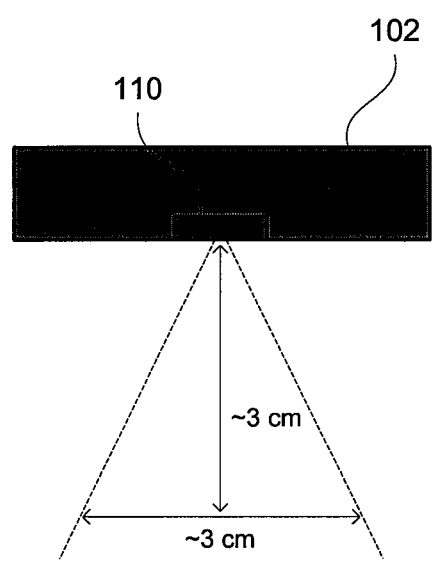
FIG. 6 shows the reception range of an exemplary fixed-focus transducer.

It is an advantageous aspect that the present systems 100 can be manufactured to minimize energy loss and thereby maximize battery life. In one particular example implementation, the C-T 102 comprises a fixed-focus transducer 110 with no steering capabilities, as shown in FIG. 6.

Another example implementation comprises a high frequency receiver 103 with a small receiver surface area and a small number of transducers. For example, receiver 103 may be an 800 kHz high frequency receiver with three transducer elements and a receiver surface area of approximately 3 mm$^2$.

In such an embodiment, the C-T 102 produces a homing signal using an array of transducers to track the location of receiver 103. It can be estimated that to produce a steering range of approximately 2 radians for a distance of approximately 3 cm, a 6×6 array of about 36 transducer elements could be used, with each transducer element having an element size of about 1 mm$^2$.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of using acoustic energy to stimulate cardiac tissue, comprising:
   subcutaneously implanting a transmitter in an intercostal space, wherein the intercostal space permits an ultrasonic imaging view of the heart:
   implanting a receiver at a first cardiac tissue location aligned with the intercostal space: wherein the receiver receives acoustic energy transmitted by the transmitter and produces a biologically stimulating electrical output in response to the received acoustic energy; and
   implanting a stimulating electrode connected to the receiver by a local lead at a second cardiac tissue location, wherein the stimulating electrode receives the biologically stimulating electrical output from the receiver and delivers said output to cardiac tissue, and wherein the first cardiac tissue location is selected to minimize the distance and angle of the acoustic energy transmission from the transmitter to the receiver and the second cardiac tissue location is selected to deliver the stimulating electrical output remote from the housing of the receiver.

2. The method of claim 1, further comprising implanting additional stimulating electrodes, wherein the stimulating electrodes are connected to the receiver by the local lead.

3. The method of claim 1, further comprising implanting additional stimulating electrodes, wherein the stimulating electrodes are connected to the receiver by additional local leads.

4. A method of stimulating cardiac tissue of a patient by converting acoustic energy to electrical energy, comprising:
   transmitting acoustic energy from a subcutaneously implanted transmitter located within an intercostal space of the patient, wherein the intercostal space permits an ultrasonic imaging view of the heart:
   receiving acoustic energy with a receiver located at a first cardiac location of the patient aligned with the intercostal space;
   producing a biologically stimulating electrical output with the receiver in response to the received acoustic energy; and
   delivering the biologically stimulating electrical output via a local lead in communication with the receiver to a stimulating electrode in communication with the local lead, the stimulating electrode implanted at a second cardiac tissue location of the patient, thereby stimulating cardiac tissue.

5. The method of claim 4, further comprising delivering the biologically stimulating electrical output to additional stimulating electrodes implanted at additional cardiac tissue locations via the local lead.

6. The method of claim 4, further comprising delivering the biologically stimulating electrical output to additional stimulating electrodes implanted at additional cardiac tissue locations via additional local leads.

* * * * *